United States Patent [19]

Hansman, Jr. et al.

[11] Patent Number: 5,039,439

[45] Date of Patent: Aug. 13, 1991

[54] OPTICALLY INDICATING SURFACE DE-ICING FLUIDS

[75] Inventors: R. John Hansman, Jr., Cambridge, Mass.; Adam Dershowitz, New York, N.Y.

[73] Assignee: Massachusetts Institute of Technology, Cambridge, Mass.

[21] Appl. No.: 325,552

[22] Filed: Mar. 17, 1989

[51] Int. Cl.⁵ ............................................. C09K 3/18
[52] U.S. Cl. ...................................... 252/70; 106/13
[58] Field of Search .................. 73/40.7, 49.2; 106/13; 252/70; 427/8, 136; 430/139

[56] References Cited

U.S. PATENT DOCUMENTS

| | | | |
|---|---|---|---|
| 3,928,654 | 12/1975 | Bonnanzio | 427/8 |
| 4,249,412 | 2/1981 | Townsend | 73/40.7 |
| 4,426,409 | 1/1984 | Roe | 252/70 |
| 4,744,913 | 5/1988 | Salvador | 252/70 |
| 4,824,588 | 4/1989 | Lin | 252/70 |

*Primary Examiner*—Paul Lieberman
*Assistant Examiner*—Alexander G. Ghyka
*Attorney, Agent, or Firm*—Hamilton, Brook, Smith & Reynolds

[57] ABSTRACT

An optically indicating de-icing solution for surfaces comprising a freezing point depressant liquid and a compound which exhibits a visually observable change as solid phase domains become present in the solution is disclosed. When applied to a surface, particularly the surface(s) of aircraft, the formation of solid phase ice domains in the liquid provides a distinct and visible change in the appearance of the solution. This allows a determination of ice formation upon the aircraft as well as a determination of the effectiveness of the de-icing solution.

11 Claims, No Drawings

OPTICALLY INDICATING SURFACE DE-ICING FLUIDS

GOVERNMENT SUPPORT

The United States Government may have rights in this invention pursuant to grants provided by the National Science Foundation and the National Aeronautics and Space Administration. The NASA Grant number assigned to this invention is NAG3-666.

BACKGROUND OF THE INVENTION

The formation of ice upon surfaces such as machinery, walkways and buildings has long been a problem when these surfaces are exposed to environments conducive to icing. For example, the effect of ice formations on the critical surfaces of aircraft can lead to severely altered aerodynamic characteristics. This can result in the inability of the aircraft to operate safely during takeoff and flight. The reduction of aerodynamic properties is evident from both wind tunnel and flight tests in which the leading edge and upper surface of wings were provided with ice formations having a thickness and roughness similar to that of sandpaper. Such icing has been found to reduce wing lift by as much as 30% and to increase drag by approximately 40%. These changes can severely reduce aircraft flight characteristics and controllability. The process of ascertaining airworthiness (i.e., a clean aircraft free of ice formations prior to takeoff) requires a team effort with the pilot making the final judgement that the aircraft is in a condition for safe flight.

Currently, the only known method for positively determining that an aircraft is free of any ice formations prior to takeoff is by close, visual inspection of its surface. A practice in use by some flight operators is to view from the cabin or cockpit critical surface areas of the aircraft (i.e., leading edges, wing surfaces and engine inlets) for indication of ice formations. In particular, recent accidents involving both large transport aircraft as well as small general aviation aircraft indicate that the current standards and methods upon which air-worthiness is based are often inadequate. Moreover, during inclement weather conditions (i.e., heavy precipitation, high wind velocity, and low ambient temperature), an observer's ability to visually note the appearance of solid phase ice domains in a partially liquid surface coating the material (i.e., a roadway, automobile, or aircraft) is often compromised.

The use of freezing point depressant (FPD) fluids to aid in ground de-icing processes and to provide a protective film to delay the formation of ice, frost and snow prior to takeoff is a method currently used by the aviation industry, as well as in treating outdoor surfaces such as walkway, roadways and driveways. U.S. Pat. No. 3,928,654 (A. J. Bonnanzio).

Despite the ability of FPD fluids to provide de-icing to critical surfaces, a need still exists for an accurate determination of the effectiveness of de-icing fluids on the critical surfaces of, for example, roadways, and machinery such as aircraft. Factors such as ambient temperature, surface temperature, concentration of de-icing fluid, rate of precipitation, and wind velocity which are difficult to instantaneously ascertain, influence the rate at which the de-icing fluids lose their effectiveness and make quantitative judgements of the condition of these surfaces exposed to low temperature environments difficult to obtain.

In particular, current visual observation methods for ascertaining ice formation on aircraft surfaces are not adequate when weather conditions are inclement and the volume of traffic is such that aircraft may be treated with de-icing fluids and then forced to wait for extended periods prior to take-off. During the period prior to takeoff, precipitation and other factors can cause de-icing fluids to become diluted, thereby reducing their FPD ability. This effect allows the formation of solid phase domains on the aircraft surface. According to FAA policy, in order to have an effective anti-icing solution on the surface prior to take-off, the freezing point of residual fluids (FPD and mixtures) should be at least about 20° below the ambient temperature or the surface temperature of the aircraft, whichever is less. However, with the addition of precipitation onto the aircraft prior to take-off, the freeze point of the liquid present on the aircraft can quickly approach the environmental temperature, thereby resulting in zones of icing.

Thus, a need exists for a de-icing method which would provide flight crews or ground personnel with a simple means for determining presence of ice, frost and snow on critical aircraft surfaces.

SUMMARY OF THE INVENTION

This invention broadly relates to novel de-icing compositions as well as to a method for optically detecting the efficacy of the de-icing solutions when applied to surfaces of any object undergoing freezing. In particularly preferred embodiments, the invention relates to novel aircraft de-icing solutions and methods for detecting ice formation on aircraft surfaces. The invention is based, in part, on the discovery that materials can be used in conjunction with de-icing chemicals that will cause a visual change in the fluid as the fluid begins to freeze.

In a broad embodiment, the de-icing composition comprises a freezing-point depressant (FPD) fluid which contains an optically detectable indicator in solution. Other compounds which optionally can be included in the solution are corrosion inhibitors and wetting agents, specific for application to an aircraft surface.

FPD fluids have the ability to lower the freezing point of a solution in order to prevent the formation of solid phase domains in the liquid phase. Preferred FPD fluids include alkylene glycols which can act as freezing point depressants even when combined with water in an aqueous solution. For use in a de-icing solution, preferred alkylene glycols include ethylene glycol, propylene glycol, diethylene glycol and mixtures thereof.

De-icing solutions of this invention comprise a material which exhibits a visually observable change when in the presence of solid phase domains in combination with the FPD liquid. Thus, if ice begins to form in the FPD liquid, the compound will undergo an optically detectable change, thereby allowing a determination of ice formation with the corresponding decrease in the FPD liquid effectiveness.

In a preferred embodiment, the optically detectable indicator material comprises a fluorescent composition. In the liquid phase, the fluorescent composition, preferably a disodium salt, can be optically detected when present at levels above a minimum concentration. Furthermore, when exposed to ultraviolet light, lower concentrations of the fluorescent composition can be detected optically. The appearance of solid phase ice domains in the liquid solution produces a distinct and visible decrease in fluorescence when compared to samples which remain entirely in the liquid phase. In a typical application, the color of the de-icing solution can vary from colorless to dark orange depending on the dye concentration and amount of solid phase present in the solution. Solid ice will not fluoresce and the color is therefore directly related to the amount of solid phase ice domains.

In the preferred method of use, the de-icing composition (i.e., solution) which contains the material capable of undergoing visually observable changes is applied to at least one surface of an object. If the visually observable compound in the de-icing solution is a fluorescent composition, the surface treated with the solution will fluoresce when few or no solid phase domains are present and when the concentration of the composition is above a minimum level. As the solution loses its FPD ability, through, for example, dilution by precipitation with concurrent ice nucleation, the material present on the treated surface will exhibit a decrease in fluorescence. Thus, a distinct difference can be optically observed between solutions containing ice domains and solutions remaining entirely in the liquid phase. Therefore, compositions and methods of this invention permit the visual determination of freezing point depressant failure.

DETAILED DESCRIPTION OF THE INVENTION

The invention is a novel de-icing solution as well as a method for optically detecting the efficacy of the de-icing solution when applied to the surface of any object whose surface may contain liquid water that is susceptible to freezing. The de-icing solution comprises a freezing point depressant and a compound capable of visually observable changes when exposed to solid phase ice domains. The FPD liquid and compound are preferably present as an aqueous solution. By exhibiting a change in appearance as solid phase domains become present in the solution, the compound provides an optical indication of the phase state of the solution and thereby allows a determination of its effectiveness as a de-icing solution.

In a preferred embodiment, the de-icing composition comprises a freezing point depressant and an optical indicator in an aqueous solution. This composition is preferably used for the surfaces of aircraft. Other compounds which optionally can be included in the de-icing solution are corrosion inhibitors, wetting agents, and materials to increase the viscosity of the solution.

Also in a preferred embodiment, the freezing point depressant comprises an alkylene glycol which can be either undiluted or in aqueous solution. The alkylene glycol is preferably diethylene glycol, ethylene glycol, propylene glycol and combinations thereof. The amount of the alkylene glycol in combination with water necessary for effective de-icing activity of the surface will vary depending upon a number of readily ascertainable external factors. These include ambient temperature, surface temperature, precipitation type and rate, relative humidity, and wind velocity and direction. A solution of between about 1 percent to about 10 percent by volume of an alkylene glycol in water is preferred.

The compound added to the freezing point depressant solution must exhibit a clear and definite visually observable change within the same temperature range as that at which the de-icing solution begins to form ice domains. Preferred compounds include fluorescent compositions which exhibit an optically detectable fluorescence change as exposure to ice domains begins. In addition to changing appearance in the presence of ice domains, the compound must also meet other criteria. For example, the compound must be environmentally inert in low concentrations and it must not exhibit detrimental interaction with the surface of the object. In the preferred embodiment of this invention, the compound is a fluorescent disodium salt (i.e. disodium fluorescein). The amount of fluorescent compound in combination with a FPD solution will vary depending upon the concentration of alkylene glycol. A concentration range of between about 0.1% and 1% by weight is preferred.

In use, the de-icing solution of this invention is applied to the object whose surface(s) are to be kept ice-free and/or whose surfaces are to be observed for the formation of ice domains. The solution is preferably sprayed, mopped, brushed, or poured onto the surface. For aircraft, this can be done repeatedly prior to takeoff to effectively clear the aircraft of all ice formations and prevent additional ice formation. Depending on the environmental conditions previously cited, the de-icing solution can be adjusted to a concentration necessary to prevent ice formation. Critical surfaces of aircraft to which the compositions of this invention can be applied, can include wing surfaces and leading edges, stabilizing devices, propellors, lift spoilers, engine inlets, fuel tanks and so on. Critical surfaces of, for example, machinery, buildings, walkways, automobiles can be determined using routine visual inspection.

The observable properties of the compound in solution with the FPD liquid provide an optical indication of the formation of ice upon the surface of any object susceptible to freezing. When present in the liquid state, the solution of the preferred disodium salt and freezing point depressant actively fluoresces. When solid phase domains become present in the liquid, the fluorescence is quenched and the solution exhibits visually observable changes in color or intensity depending on the concentration of the compound.

In a preferred embodiment of this invention, a fluorescein di-sodium salt is added to a solution of ethylene glycol. In the fluid state, the dyed glycol-water mixture has a yellow color and actively fluoresces. When the mixture freezes, the fluorescene is quenched and the resulting ice becomes either clear or dark orange, depending on the concentration of dye. In addition, under UV light, there is a dramatic and distinct difference between the frozen and unfrozen regions.

The source of ultra violet light can be a portable or permanent apparatus located on, or near the object. In the case aircraft, the light source can be located on each runway or mounted on the aircraft itself.

Surfaces treated with the fluorescent de-icing fluid with or without exposure to ultra violet light can be viewed visually or photographically for the presence of fluorescent activity. Another observation method particularly useful for aircraft is the use of a video camera mounted on the aircraft or at the edge of the runway and connected to a video display apparatus located in the control tower or cockpit of the aircraft. Such a configuration would allow the flight crew or ground personnel to determine the presence of ice from a remote location.

Another method for determining the presence of ice utilizes a programmed optoelectronic device. Such a device can be used to scan the surface(s) of the object (e.g., an aircraft) and measure the presence of de-icing solution on treated surfaces. Furthermore, specific spectral lines emitted by the fluorescing compound can also be measured. If a fluorescent composition is used as the visually observable compound, fluorescence levels can be determined and relayed to the flight crew or control personnel thereby allowing a determination of the presence of ice on the object's surface. This invention will now be further described by reference to the following, non-limiting Example.

EXAMPLE: TESTS OF OPTICAL INDICATORS FOR DE-ICING FLUIDS

A: Disodium fluorescein in water

Fluorescein di-sodium salt was added to distilled water which was subsequently frozen. Ratios ranged from 1 to 10 parts of fluorescein salt to 1000 parts of water by weight. These concentrations were tested in 5 cm×7 cm plastic containers. The liquid was put into the bottoms of the containers in layers of between 0.2–2 cm. The dye-water solution had a characteristic yellow color and fluoresced brightly under UV light. When the dye-water mixture was frozen, it stopped fluorescing as observed under UV light and became brownish-red under visible light.

B. Disodium fluorescein in FPD fluid

When ethylene-glycol solution was added, the concentration of fluorescein dye was found to be more critical in order to retain the dependance of fluorescence on phase change. A higher fluorescein concentration in the range of 1 part in 100 was used. At high ratios of ethylene-glycol solution approaching 25 percent (v/v in water), the mixtures would not freeze solid at −18° C. At lower glycol concentrations ranging from 1 percent to 10 percent, the FPD liquid would freeze and stopped fluorescing when solid.

EQUIVALENTS

Those skilled in the art will recognize or be able to ascertain, using no more than routine experimentation, many equivalents to the specific embodiments described herein. Such equivalents are intended to be encompassed by the following claims.

We claim:

1. A method for determining and preventing the formation of ice upon aircraft, the method comprising:
   a) applying to at least one surface of an aircraft a solution which comprises:
      i) a liquid comprising a freezing point depressant; and
      ii) a fluorescent compound which exhibits a visually observable change as solid phase ice domains become present in the solution; and
   b) optically detecting changes in the solution to thereby determine the phase state of the solution upon the aircraft.

2. A method of claim 1 wherein the solution is applied by a process selected from the group consisting of spraying, brushing, pouring and mopping.

3. A method of claim 1 wherein the freezing point depressant comprises an alkylene glycol.

4. A method of claim 3 wherein the alkylene glycol is selected from the group consisting of diethylene glycol, ethylene glycol, propylene glycol and effective combinations thereof.

5. A method of claim 1 wherein the freezing point depressant is present as an aqueous solution.

6. A method of claim 1 wherein the fluorescent compound comprises a disodium salt.

7. A method of claim 1 wherein at least one surface of the aircraft is exposed to ultraviolet radiation during the optical detection step.

8. A method of claim 1 wherein the optical detection comprises visual observation of at least one surface of the aircraft.

9. A method of claim 1 wherein the optical detection is carried out using photographic means.

10. A method of claim 1 wherein the optical detection is carried out using video means.

11. A method of claim 1 wherein the optical detection is carried out using an optoelectronic device.

* * * * *